(12) United States Patent
Uchida

(10) Patent No.: US 9,221,562 B2
(45) Date of Patent: Dec. 29, 2015

(54) APPARATUS FOR INSPECTING FILLER IN CONTAINER, APPARATUS FOR FILLING FILLER, AND METHOD FOR INSPECTING FILLER IN CONTAINER

(75) Inventor: Toyokazu Uchida, Tokyo (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 284 days.

(21) Appl. No.: 13/991,474

(22) PCT Filed: Mar. 1, 2012

(86) PCT No.: PCT/JP2012/055196
§ 371 (c)(1),
(2), (4) Date: Jun. 4, 2013

(87) PCT Pub. No.: WO2012/118141
PCT Pub. Date: Sep. 7, 2012

(65) Prior Publication Data
US 2013/0255832 A1   Oct. 3, 2013

(30) Foreign Application Priority Data

Mar. 3, 2011   (JP) ................................. 2011-046551

(51) Int. Cl.
*B65B 3/04* (2006.01)
*G01N 1/02* (2006.01)
(Continued)

(52) U.S. Cl.
CPC .. *B65B 3/04* (2013.01); *G01N 1/02* (2013.01); *G01N 5/02* (2013.01); *G01N 9/02* (2013.01); *G01N 35/0099* (2013.01); *G01N 35/00009* (2013.01)

(58) Field of Classification Search
CPC ............ B65B 57/00; G01N 1/10; G01N 1/14; G01N 2001/1031; G01N 2035/00108; G01N 2223/639
USPC .................... 141/82, 83, 94, 98; 53/471, 281; 73/19.1, 864
See application file for complete search history.

(56) References Cited

U.S. PATENT DOCUMENTS 3,902,852 A * 9/1975 Lemieux et al. ............ 73/863.32
4,066,412 A * 1/1978 Johnson et al. ................. 422/65

(Continued)

FOREIGN PATENT DOCUMENTS

JP          50-1795          1/1975
JP          57-53640         3/1982

(Continued)

OTHER PUBLICATIONS

International Search Report issued May 22, 2012 in International (PCT) Application No. PCT/JP2012/055196 with English Translation.

(Continued)

*Primary Examiner* — Nicolas A Arnett
(74) *Attorney, Agent, or Firm* — Wenderoth, Lind & Ponack, L.L.P.

(57) ABSTRACT

A container filler-inspecting apparatus includes a weight-measuring unit (14) that measures the weight of the container (1) filled with a filler (S1), a sample-extracting unit (12) that extracts a fixed amount of filler (S1) from a tip opening (2) of the container (1), and a sampling unit (13) that performs a sampling operation by wiping off the filler extracted by the sample-extracting unit (12) with a sampling paper sheet.

5 Claims, 8 Drawing Sheets

(51) Int. Cl.
  *G01N 5/02* (2006.01)
  *G01N 9/02* (2006.01)
  *G01N 35/00* (2006.01)

(56) References Cited

U.S. PATENT DOCUMENTS

| | | | | |
|---|---|---|---|---|
| 5,062,292 | A | * | 11/1991 | Kanba et al. .................. 73/19.01 |
| 5,148,841 | A | * | 9/1992 | Graffin ............................ 141/83 |
| 5,460,057 | A | * | 10/1995 | Ostrup ....................... 73/864.81 |
| 5,563,384 | A | | 10/1996 | Marlow et al. |
| 2005/0060962 | A1 | * | 3/2005 | Rothbauer et al. .............. 53/471 |
| 2010/0288040 | A1 | | 11/2010 | Jorgensen |

FOREIGN PATENT DOCUMENTS

| | | |
|---|---|---|
| JP | 62-134047 | 8/1987 |
| JP | 3-69495 | 3/1991 |
| JP | 06-191055 | 7/1994 |
| JP | 8-43537 | 2/1996 |
| JP | 2002-211514 | 7/2002 |
| JP | 2006-8161 | 1/2006 |
| JP | 2010-201287 | 9/2010 |

OTHER PUBLICATIONS

Written Opinion of the International Searching Authority issued May 22, 2012 in International (PCT) Application No. PCT/JP2012/055196 with English Translation.

Office Action issued Feb. 3, 2015 in corresponding Japanese Patent Application No. 2011-046551 (with English translation).

Extended European Search Report issued Jul. 24, 2014 in corresponding European Patent Application 12752364.5.

\* cited by examiner

APPARATUS FOR INSPECTING FILLER IN CONTAINER, APPARATUS FOR FILLING FILLER, AND METHOD FOR INSPECTING FILLER IN CONTAINER

TECHNICAL FIELD

The present invention relates to a container filler-inspecting apparatus, a filling apparatus, and a container filler-inspecting method which can inspect a filler with which a container is filled.

Priority is claimed on Japanese Patent Application No. 2011-046551, filed Mar. 3, 2011, the content of which is incorporated herein by reference.

BACKGROUND ART

Conventionally, a two-liquid mixing type method of mixing a first raw material and a second raw material to form a sealant or an adhesive is known. This two-liquid mixing type of sealant or adhesive is used as sealing or bonding means for filling gaps of connecting parts or joints of various structures such as an aircraft. In this two-liquid mixing type of sealant, a first raw material and a second raw material individually have liquidity at room temperature. However, when two raw materials are mixed once, a curing reaction is started and the mixture is cured after a predetermined time. However, the mixing of the first raw material and the second raw material for every work operation using the two-liquid mixing type of sealant or the like lowers work efficiency. Accordingly, the first raw material and the second raw material are mixed in advance in low-temperature circumstances to form a two-liquid mixing type of sealant, containers are rapidly filled with the two-liquid mixing type of sealant, and the containers are quickly frozen and are then stored in a freezer. At the time of use, the two-liquid mixing type of sealant is used by taking out the containers from the freezer and defrosting them.

A sealant-filling apparatus for filling a container with a two-liquid mixing type of sealant is known which includes a first feed unit that feeds a first raw material through a first flow channel and a second feed unit that feeds a second raw material through a second flow channel (for example, see PTL 1). The sealant-filling apparatus includes a third flow channel into which the first flow channel and the second flow channel are merged and through which the first raw material and the second raw material pass. The sealant-filling apparatus mixes at least two kinds of raw materials. A mixer for mixing the first raw material and the second raw material is disposed in the third flow channel, and the mixed material obtained from the mixer is discharged through a fourth flow channel. The sealant-filling apparatus includes a system pressure reducer that causes at least the mixer to be a pressure-reduced atmosphere before mixing the first raw material and the second raw material.

The sealant-filling apparatus respectively agitates the first raw material and the second raw material under reduced pressure before mixing the first raw material and the second raw material. Then, by mixing the first raw material and the second raw material after causing the mixer to enter the pressure-reduced atmosphere, the mixing of air in the course of mixing is reduced and no burst occurs when the resultant sealant is ejected from a cartridge.

CITATION LIST

Patent Literature

[PTL 1] Japanese Patent Application, First Publication No. 2010-201287

SUMMARY OF INVENTION

Problem to be Solved by the Invention

However, in the sealant-filling apparatus disclosed in PTL 1, air may be mixed into the sealant when filling a cartridge as a container with the sealant as a filler. When air is mixed into the sealant, a burst occurs at the time of ejecting the filler from the container. Accordingly, there is a demand for an inspection apparatus and method which can easily inspect whether a container is appropriately filled with a filler without mixing air.

The invention is made to solve the above-mentioned problems, and an object thereof is to provide a container filler-inspecting apparatus, a filling apparatus, and a container filler-inspecting method, which can easily inspect a filler with which a container is filled.

Means for Solving the Problem

According to an aspect of the invention, a container filler-inspecting apparatus is provided for inspecting a filler with which a container is filled by a fixed amount, including: a weight-measuring unit that measures the weight of the container filled with the filler; a sample-extracting unit that extracts a fixed amount of filler from a tip opening of the container; and a sampling unit that performs a sampling operation by wiping off the filler extracted by the sample-extracting unit with a sampling paper sheet.

According to this configuration, the mixing state of air can be determined by measuring the weight of the container filled with the filler through the use of the weight-measuring unit. This is because in the case where the container is appropriately filled with the filler, the weight of the container differs from that in the case where air is mixed with the filler. The sample-extracting unit extracts a fixed amount of filler as a sample from the tip opening of the container, and the sampling unit wipes out the extracted filler with the sampling paper sheet. Accordingly, by examining the characteristics of the filler sampled with the sampling paper sheet, the characteristics of the filler with which the container is filled can be determined and the mixing state of air into the filler can be seen from the characteristics.

In the container filler-inspecting apparatus, the sampling unit may include a wiping unit that forms a folded portion in the sampling paper sheet by folding the sampling paper sheet, and may wipe off the filler with the sampling paper sheet by causing the container to move relative to the wiping unit.

According to this configuration, the wiping unit can wipe off the extracted filler with the sampling paper sheet to perform the sampling operation.

In the container filler-inspecting apparatus, the sampling unit may sample the filler from a plurality of the containers filled with the filler while sequentially changing positions of the containers above the sampling paper sheet in a width direction and a length direction thereof.

According to this configuration, it is possible to sample plural fillers with the sampling paper sheet.

According to another aspect of the invention, there is provided a filling apparatus including: the container filler-inspecting apparatus; a filling unit that fills the container with the filler; and a capping unit that caps the tip opening of the container filled with the filler.

According to this configuration, it is possible to cap the tip opening to enclose the filler through the use of the capping unit while inspecting whether the filling unit appropriately fills the container with the filler by the use of the container filler-inspecting apparatus.

According to still another aspect of the invention, there is provided a container filler-inspecting method for inspecting a filler with which a container is filled by a fixed amount, including: a weight-measuring step of measuring the weight of the container filled with the filler; a sample-extracting step of extracting a fixed amount of filler from a tip opening of the container; and a sampling step of performing a sampling operation by wiping off the filler extracted in the sample-extracting step with a sampling paper sheet.

According to this method, the mixing state of air can be determined by measuring the weight of the container filled with the filler through the use of the weight-measuring step. This is because in the case where the container is appropriately filled with the filler, the weight of the container differs from the weight of a container in the case where air is mixed with the filler. In the sample-extracting step, a fixed amount of filler as a sample is extracted from the tip opening of the container. In the sampling step, the extracted filler is wiped out with the sampling paper sheet. Accordingly, by examining the characteristics of the filler sampled with the sampling paper sheet, the characteristics of the filler with which the container is filled can be determined and the mixing state of air into the filler can be seen from the characteristics.

Effects of the Invention

By using the container filler-inspecting apparatus and the container filler-inspecting method according to the invention, it is possible to easily inspect a filler with which a container is filled.

By using the filling apparatus according to the invention, it is possible to fill a container with a filler while easily inspecting the filler.

DESCRIPTION OF EMBODIMENTS

Hereinafter, a sealant-filling apparatus and a sealant-filling method according to an embodiment of the invention will be described with reference to the accompanying drawings.

The sealant-filling apparatus which is a filling apparatus according to this embodiment serves to fill a container with a two-liquid mixing type of sealant as a filler.

Figure 1:
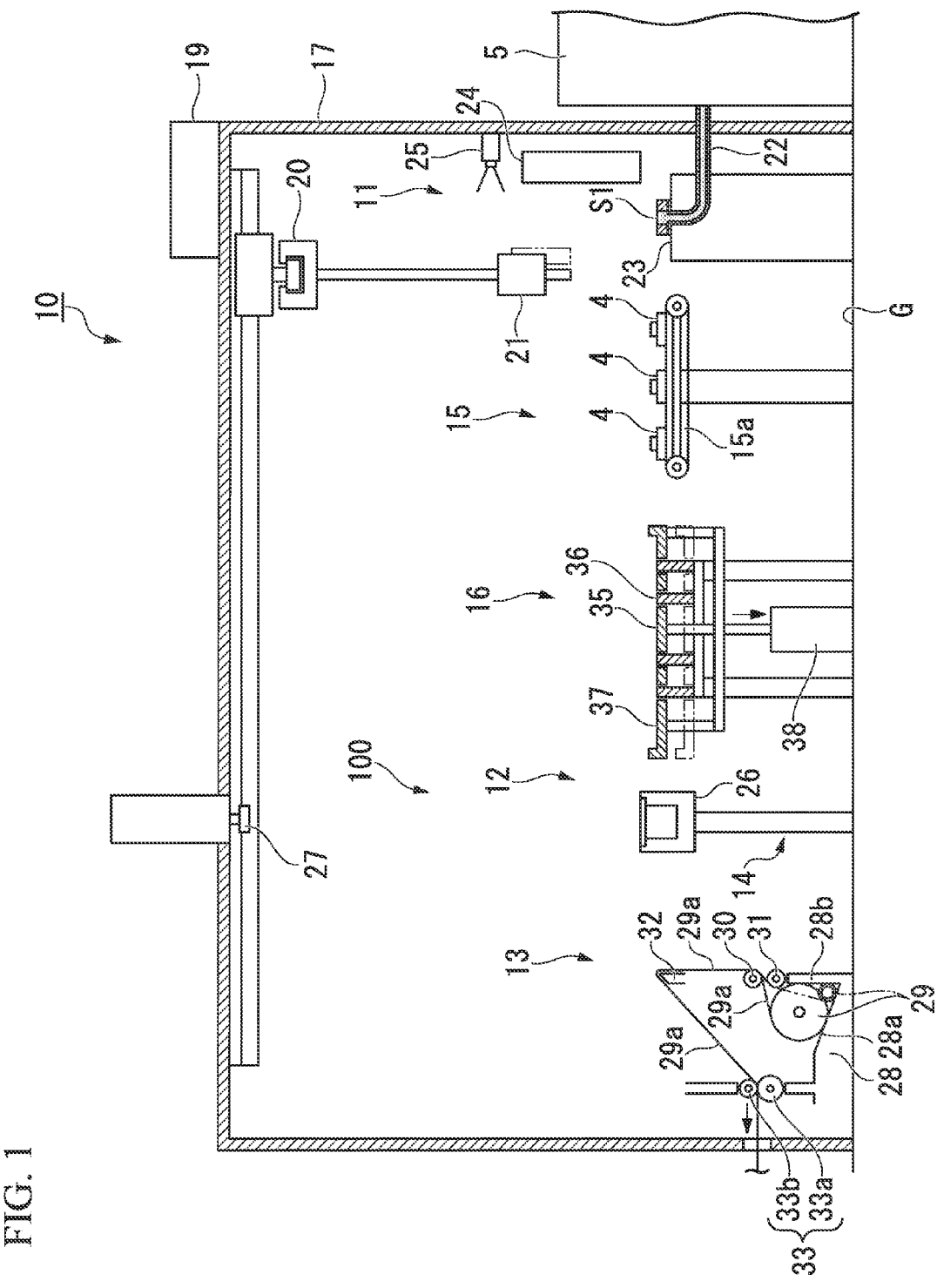
FIG. 1 is a side view schematically illustrating a sealant-filling apparatus for performing a sealant-filling method according to an embodiment of the invention.

As shown in FIG. 1, a sealant-filling apparatus 10 for performing a sealant-filling method according to an embodiment of the invention includes a filling unit 11 that fills a container 1 (see FIG. 3) with a sealant S1, a sealant-inspecting apparatus (container filler-inspecting apparatus) 100 that inspects the sealant S1 with which the container 1 is filled, a capping unit 15 that caps the container 1, a container-discharging unit 16 that discharges the container 1 filled with the sealant S1, a controller 19 that controls the units, a case 17 that houses the units, and a freezing unit (not shown) that freezes the inside of the case 17. The sealant-inspecting apparatus 100 includes a sample-extracting unit 12, a sampling unit 13, and a weight-measuring unit 14.

A two-liquid mixture freezer 5 connected to the filling unit 11 and a storage unit (see FIG. 2) 6 connected to the container-discharging unit 16 are disposed outside the sealant-filling apparatus 10. The two-liquid mixture freezer 5 stores two kinds of sealants serving as a first raw material and a second raw material to fill the container 1. The two kinds of sealants are mixed and are fed as a sealant S1 to the filling unit 11 via a duct 22. The container 1 used in the sealant-filling apparatus 10 according to this embodiment is labeled in advance at room temperature and a unique identification mark is printed as a number or a barcode. Accordingly, when the container 1 is carried into the case 17 frozen by a not-shown freezing unit and dew condensation water is generated on the surface of the container 1, the container is labeled in advance and thus the label will not be detached therefrom due to attachment failure.

The filling unit 11, the sample-extracting unit 12, the sampling unit 13, the weight-measuring unit 14, the capping unit 15, and the container-discharging unit 16 are disposed on the top surface of a base G. The sealant-filling apparatus 10 includes a three-axis robot 20 that is disposed in the upper part of the case 17 so as to be movable in a vertical direction and two horizontal directions perpendicular thereto. A robot hand 21 of the three-axis robot 20 holds the container 1.

Figure 3:
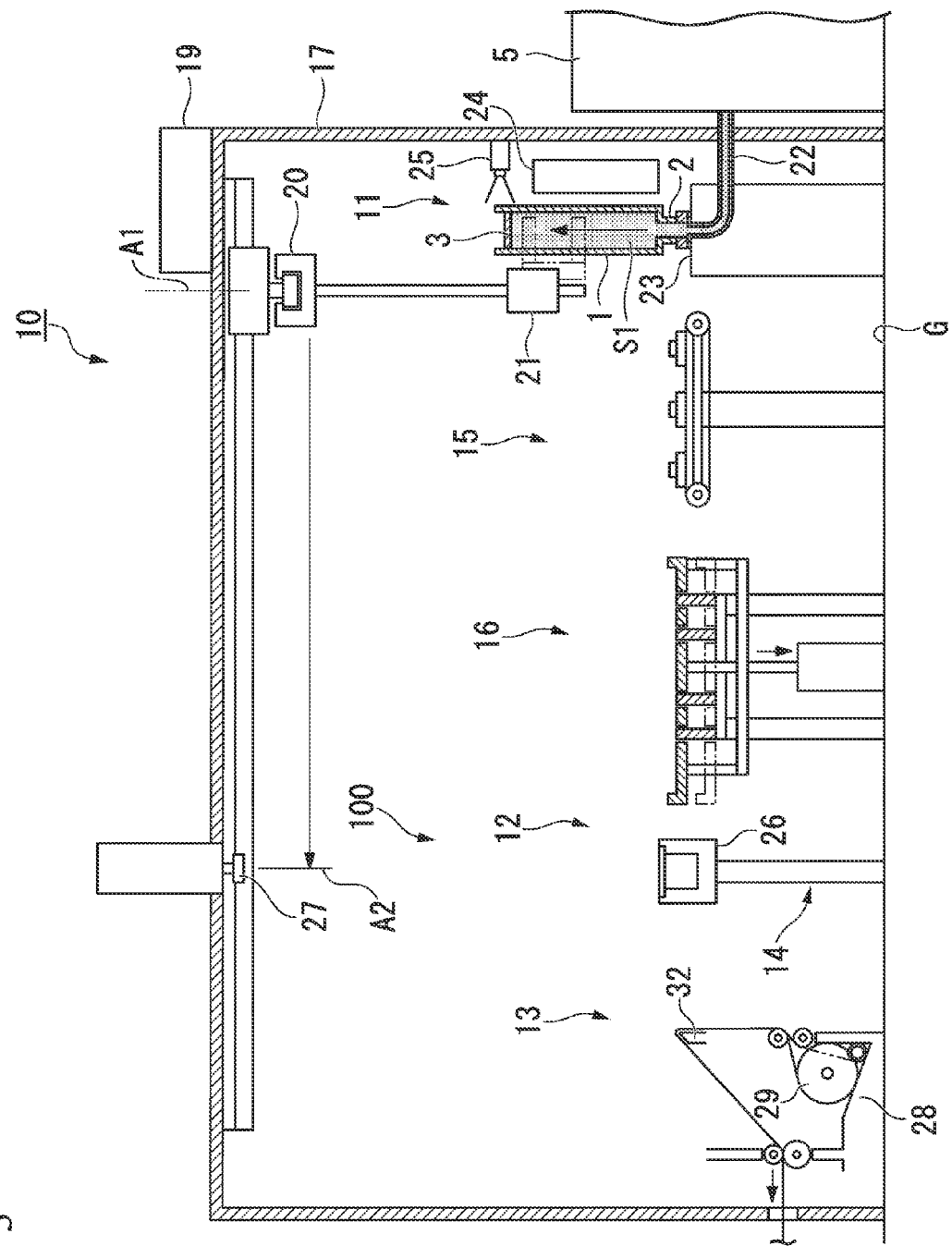
FIG. 3 is a side view schematically illustrating a filling step of a sealant-filling method performed by the sealant-filling apparatus shown in FIG. 1.

The filling unit 11 includes a filling platform 23 communicating with the duct 22, a mark reader 24, and a camera 25 disposed on the side of the filling platform 23. As shown in FIG. 3, when the container 1 with an inverted posture in which the tip opening 2 faces down is placed on the filling platform 23 by the robot hand 21, the filling unit 11 reads the identification mark printed on the label of the container 1 through the use of the mark reader 24.

The filling unit 11 fills the container with the sealant S1 from the tip opening 2 of the container 1 through the use of the filling platform 23 until an inside plug 3 of the container 1 reaches a fixed position. As shown in FIG. 3, when the container is filled with the sealant S1, the filling unit 11 detects the position of the inside plug 3 by using the camera 25. The camera 25 is connected to the controller 19. The controller 19 stores the position of the inside plug 3 in advance where the container 1 is filled with a predetermined amount of sealant S1. The controller 19 controls the filling unit 11 to fill the container 1 with the sealant S1 until the inside plug 3 reaches the position where the container is filled with a predetermined amount on the basis of an image input from the camera 25.

Figure 4:
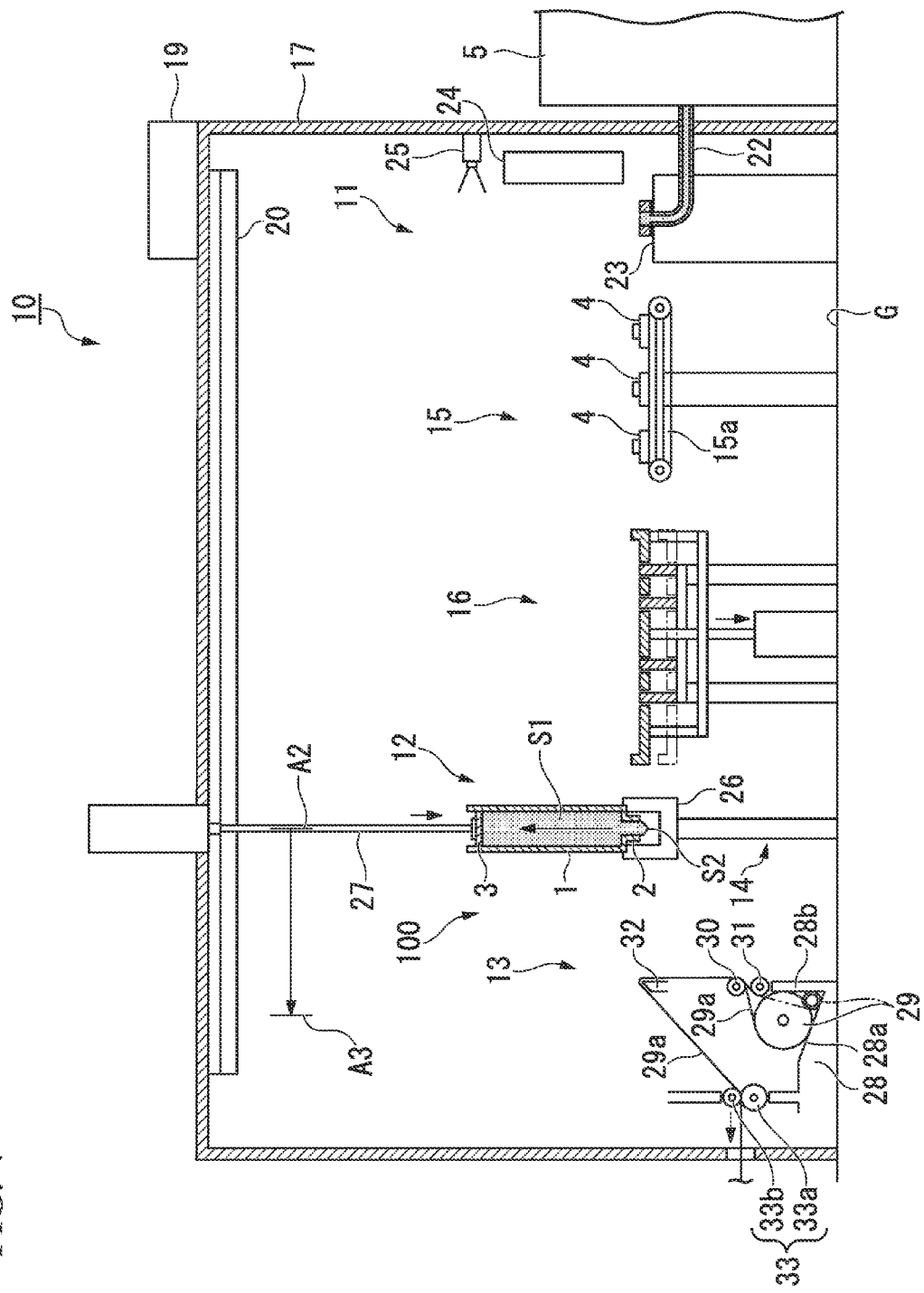
FIG. 4 is a side view schematically illustrating a sample-extracting step of the sealant-filling method performed by the sealant-filling apparatus shown in FIG. 1.

The sample-extracting unit 12 includes a platform 26 holding the tip opening 2 with the inverted posture in which the tip opening 2 of the container 1 faces down as shown in FIG. 4. The sample-extracting unit 12 causes a pressing member 27 to move down under the control of the controller 19 in a state where the container 1 is placed on the platform 26. As the pressing member 27 moves down and presses down the inside plug 3 from above, the sample-extracting unit 12 extracts a predetermined amount of sample sealant S2 from the tip opening 2.

The weight-measuring unit 14 is, for example, a load cell built in the lower part of the platform 26 and measures the weight of the container 1 placed on the platform 26 as shown in FIG. 4. The weight measured by the weight-measuring unit 14 is output to the controller 19 and is stored in the controller 19 in correlation with data read by the mark reader 24. As described above, since the filling unit 11 fills the container while managing the position of the inside plug 3 through the use of the camera 25, the container is filled with a fixed amount of sealant S1. Therefore, where air is mixed into the container 1, the weight measured by the weight-measuring unit 14 decreases. Accordingly, the amount of air mixed in the sealant S1 with which the container 1 is filled can be inspected on the basis of the measurement result of the weight-measuring unit 14.

The sampling unit 13 includes a roll-housing unit 28 in which a paper roll 29 with a sampling paper sheet 29a wound is rotatably housed, a pair of guide rollers 30 and 31 that is disposed both on the upper and the lower side of the sampling paper sheet 29a drawn from the paper roll 29 and that guides upward the sampling paper sheet 29a, a wiping unit 32 that folds down the sampling paper sheet 29a which has been guided upward by the pair of guide rollers 30 and 31, and a drawing unit 33 that draws the sampling paper sheet 29a from the paper roll 29.

The roll-housing unit 28 includes an inclined portion 28a having an inclined surface and a wall portion 28b disposed upright from the bottom of the inclined portion 28a. The paper roll 29 is rotatably supported by the inclined portion 28a and the wall portion 28b. The drawing unit 33 includes a drive roller 33a, a pinch roller 33b pinching the sampling paper sheet 29a along with the drive roller 33a, and a driving unit (not shown) that drives the drive roller 33a to rotate.

Figure 5:
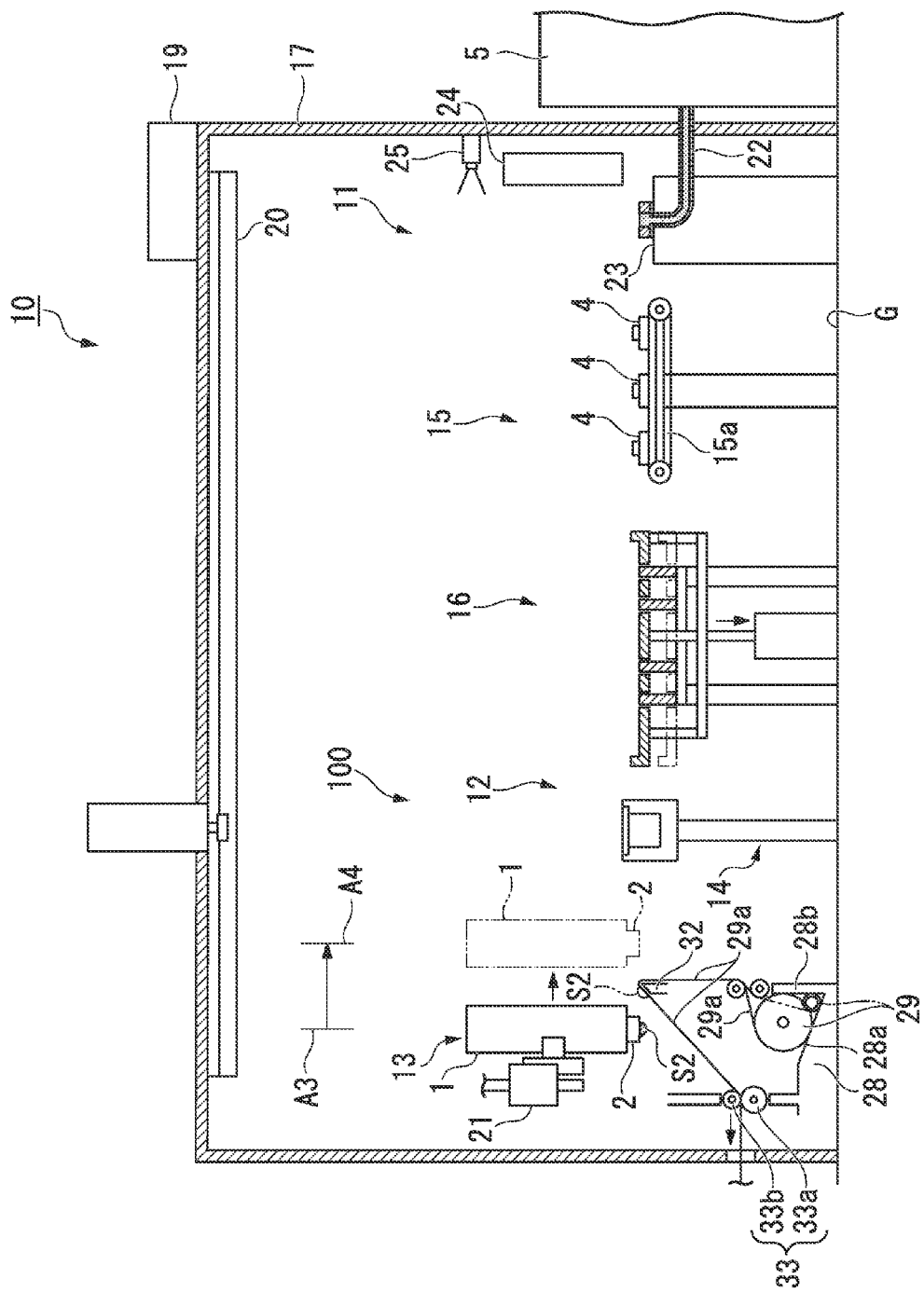
FIG. 5 is a side view schematically illustrating an inspection step of the sealant-filling method performed by the sealant-filling apparatus shown in FIG. 1.

The sampling unit 13 can wipe off the sample sealant S2, which has been extracted by a predetermined amount from the tip opening 2 of the container 1, with the sampling paper sheet 29a folded by the wiping unit 32, as shown in FIG. 5, by causing the container 1 held by the robot hand 21 to move relative to the wiping unit 32 through the use of the three-axis robot 20. The sample sealant S2 wiped out with and attached to the sampling paper sheet 29a is sequentially carried to the outside of the sealant-filling apparatus 10 along with the sampling paper sheet 29a by the drawing unit 33.

At this time, the operation of sampling the sample sealant S2 with the sampling paper sheet 29a is performed at a predetermined pitch in the width direction of the sampling paper sheet 29a (the depth direction of FIG. 1) and at a predetermined pitch in the length direction of the sampling paper sheet 29a (the direction in which it is drawn out by the drawing unit 33). Outside the sealant-filling apparatus 10, the attached sample sealant S2 is removed from the sampling paper sheet 29a, and the amount of air mixed in the sealant S1 with which the container is filled is inspected on the basis of the elastic force or the variation in shape before and after the curing by the use of a not-shown tester. For example, where the amount of air mixed is large, the elastic coefficient of the sample sealant S2 is lowered due to the influence of the mixed air. The sample sealant S2 extracted by a predetermined amount and wiped out in a substantially fixed shape is cured when it is taken out of the container 1. Where the amount of air mixed is large, the sample sealant is deformed after being cured at a high shrinkage rate due to pores included therein. Therefore, the sampling unit 13 can inspect the amount of air mixed in the sealant S1 with which the container 1 is filled on the basis of the elastic force or shape of the sample sealant S2 by inspecting a predetermined amount of sample sealant S2 extracted. Since the sampling unit 13 wipes out a predetermined amount of sample sealant S2 extracted by the sample-extracting unit 12, a complex apparatus configuration is not necessary, and it is possible to simply perform sampling and inspection at low cost, thereby easily performing total inspection on the containers 1 filled with the sealant S1.

Figure 7:
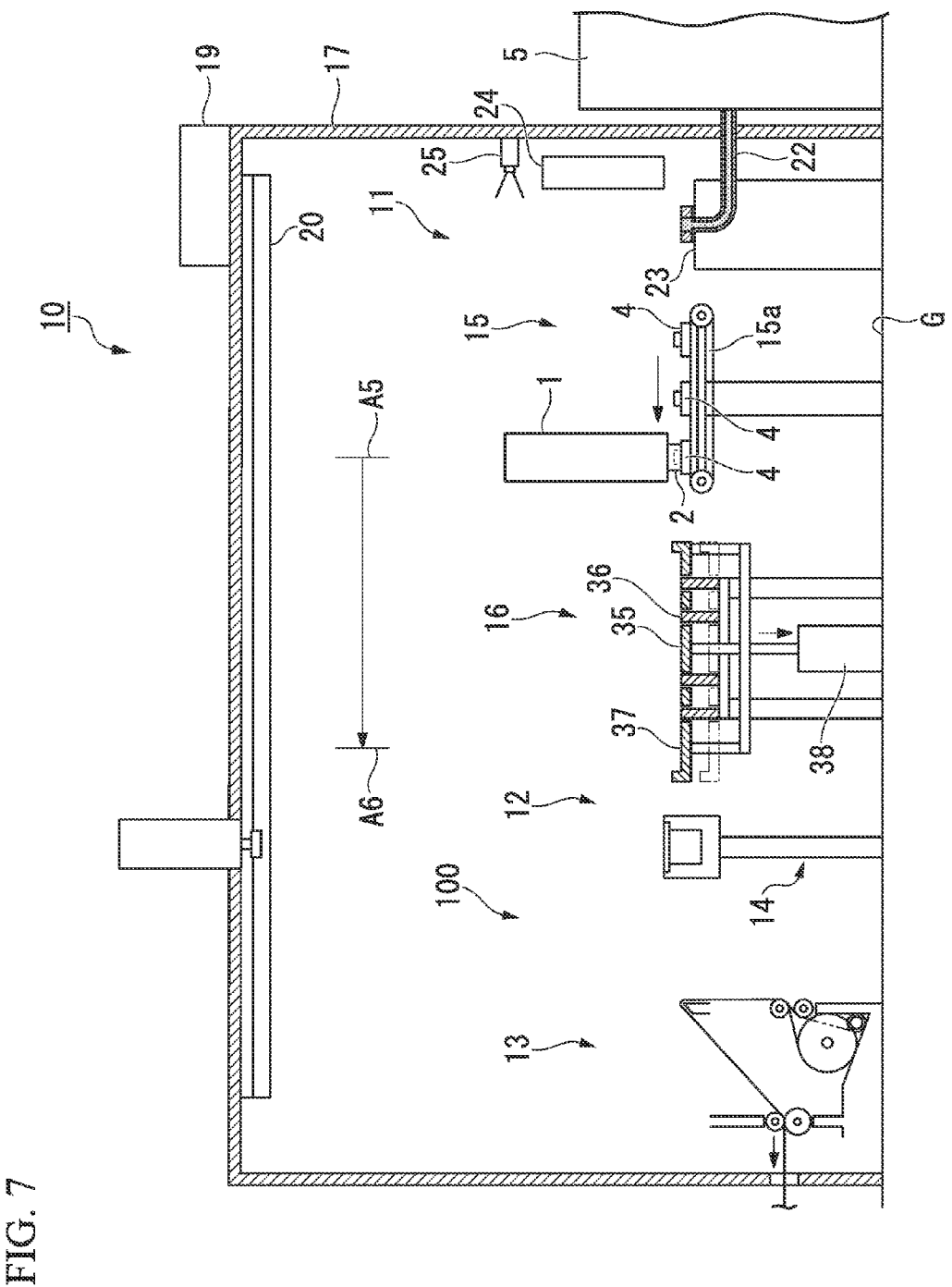
FIG. 7 is a side view schematically illustrating a capping step of the sealant-filling method performed by the sealant-filling apparatus shown in FIG. 1.

The capping unit 15 conveys plural caps 4 by using a belt conveyor 15a, as shown in FIG. 7. A container 1 with the inverted posture in which the tip opening 2 faces down is carried by the three-axis robot 20 and goes down to the cap 4, whereby the tip opening 2 is covered with the cap 4.

When storing the container 1 in the storage unit 6 (see FIG. 2), the container-discharging unit 16 changes the posture of the container 1 from the inverted posture in which the tip opening 2 faces down to the horizontal posture and discharges the container 1. The container-discharging unit 16 includes a first support portion 35 formed in a comb shape and a second support 36 disposed between the comb teeth of the first support portion 35.

Figure 8:
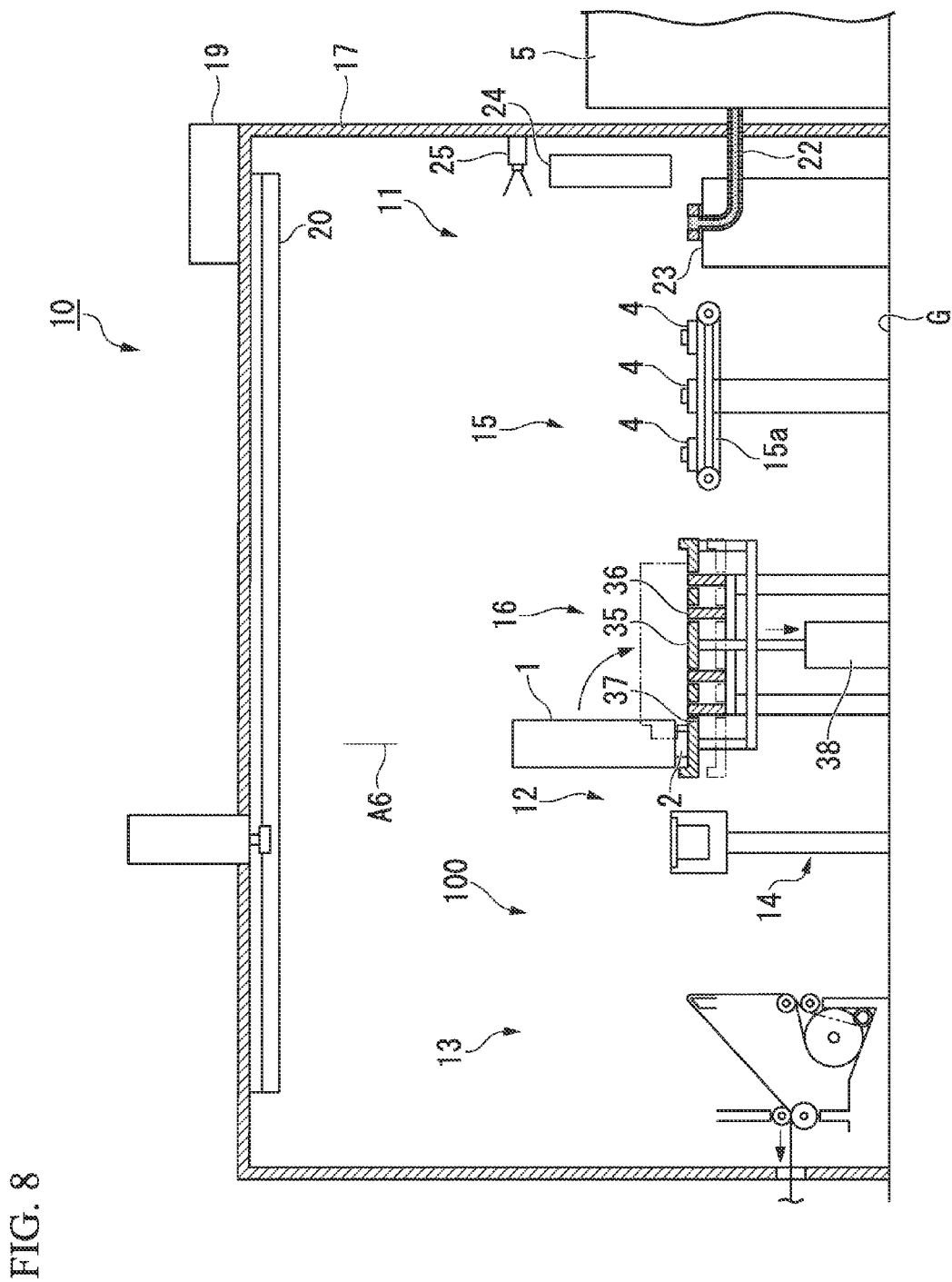
FIG. 8 is a side view schematically illustrating a direction-changing step of the sealant-filling method performed by the sealant-filling apparatus shown in FIG. 1.

As shown in FIG. 8, the first support portion 35 includes a falling concave portion 37 in which the cap 4 of the container 1 carried by the three-axis robot 20 is disposed. The falling concave portion 37 moves down so as to expose the second support portion 36 by the driving unit 38. The second support portion 36 is disposed between the comb teeth of the first support portion 35 and is inclined down to a not-shown outlet of the container 1. When the first support portion 35 moves down, the container 1 is passed to the second support portion 36. In the container-discharging unit 16, the container 1 with the inverted posture in which the tip opening 2 faces down is placed on the falling concave portion 37 of the first support portion 35 and the side portion of the cap 4 is dropped on the falling concave portion 37. The container-discharging unit 16 changes the posture of the container 1 to the horizontal posture on the first support portion 35. The container-discharging unit 16 passes the container 1 to the second support portion 36 when the first support portion 35 moves down by the use of the driving unit 38 under the control of the controller 19. The container 1 rolls along the inclination of the second support portion 36 and is discharged to the external storage unit 6 through a not-shown outlet.

Figure 2:
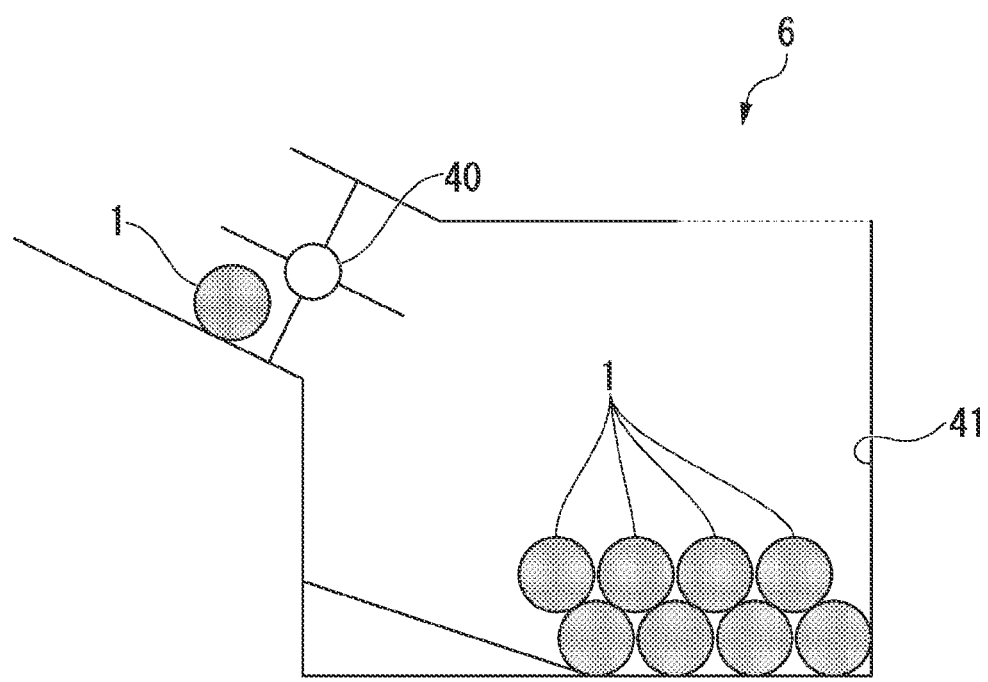
FIG. 2 is a side view schematically illustrating a storage applied to the sealant-filling apparatus shown in FIG. 1.

As shown in FIG. 2, the storage unit 6, the temperature of which is managed, includes a revolving door 40 through which the container 1 of which the posture is changed to the horizontal posture is carried and a cold storage 41 disposed downstream side of the revolving door 40.

The storage unit 6 stores the container 1 rolling and being carried through the second support portion 36 of the container-discharging unit 16 in the cold storage 41 with the temperature maintained by the revolving door 40. Therefore, the container 1 filled with a predetermined amount of sealant S1 is stored in the cold storage 41 of which the temperature is managed to a temperature at which the sealant S1 after two liquids are mixed is not cured in the storage unit 6. Accordingly, the storage unit 6 can store the container 1 with characteristics satisfactorily maintained without curing the sealant S1.

A sealant-filling method which is the filler filling method performed by the sealant-filling apparatus 10 will be described. The following steps are performed under the control of the controller 19.

As shown in FIG. 3, the filling step is performed at the position A1 of the three-axis robot 20.

In the filling step, a container 1 with an inverted posture in which the tip opening 2 faces down by using the robot hand 21 is filled with the sealant S1, which has been fed through the duct 22 from the two-liquid mixture freezer 5, through the tip opening 2 thereof. At the same time, the identification mark printed on the label of the container 1 is read by the mark reader 24 and the reading result is output to the controller 19. Under the control of the controller 19, the container 1 is filled with a predetermined amount of sealant S1 by the filling unit 11 up to the position of the inside plug 3 detected by the camera 25. When the filling step is ended, the controller 19 causes the container 1 filled with the sealant S1 to move to a next position A2 through the use of the three-axis robot 20.

As shown in FIG. 4, a sample-extracting step is performed at the position A2 of the three-axis robot 20.

In the sample-extracting step, the controller 19 places the container 1 with the inverted posture in which the tip opening 2 faces down on the platform 26 by the use of the three-axis robot 20. Then, the controller 19 causes the pressing member 27 to move down and to presses the inside plug 3 of the container 1 from above, thereby extracting a fixed amount of sample sealant S2. The amount of sample sealant S2 extracted is very small so as not to flow down.

At this time, a weight-measuring step is performed. In the weight-measuring step, the weight of the container 1 is measured by the weight-measuring unit 14. The weight measured by the weight-measuring unit 14 is output to the controller 19 and is stored in the controller 19 in correlation with the data read by the mark reader 24. Accordingly, the controller 19 can identify what container 1 is accepted or rejected on the basis of the measured weight.

When the sample-extracting step and the weight-measuring step are ended, the container 1 containing the sample sealant S2 of which a fixed amount is extracted moves to a next position A3 along with the three-axis robot 20.

As shown in FIG. 5, a sampling step is performed between the position A3 and the position A4 of the three-axis robot 20.

In the sampling step, under the control of the controller 19, a fixed amount of sample sealant S2 is wiped out from the tip opening 2 of the container 1 with the inverted posture in which the tip opening 2 faces down by the use of the sampling paper sheet 29a drawn out of the roll-housing unit 28. Specifically, the height of the tip opening 2 of the container 1 carried to the position A3 is set to be substantially equal to the height of the folded point of the sampling paper sheet 29a folded by the wiping unit 32 by the use of the three-axis robot 20. The position in the width direction of the container 1 is set to a predetermined position on the sampling paper sheet 29a by the use of the three-axis robot 20. The container 1 moves from the position A3 which is on one side of the wiping unit 32 through the wiping unit 32 to the position A4 which is on the other side thereof by the use of the three-axis robot 20. Accordingly, the sample sealant S2 extracted from the tip opening 2 is wiped out with the sampling paper sheet 29a folded by the wiping unit 32 which is located substantially at the same height as the tip opening 2.

Figure 6:
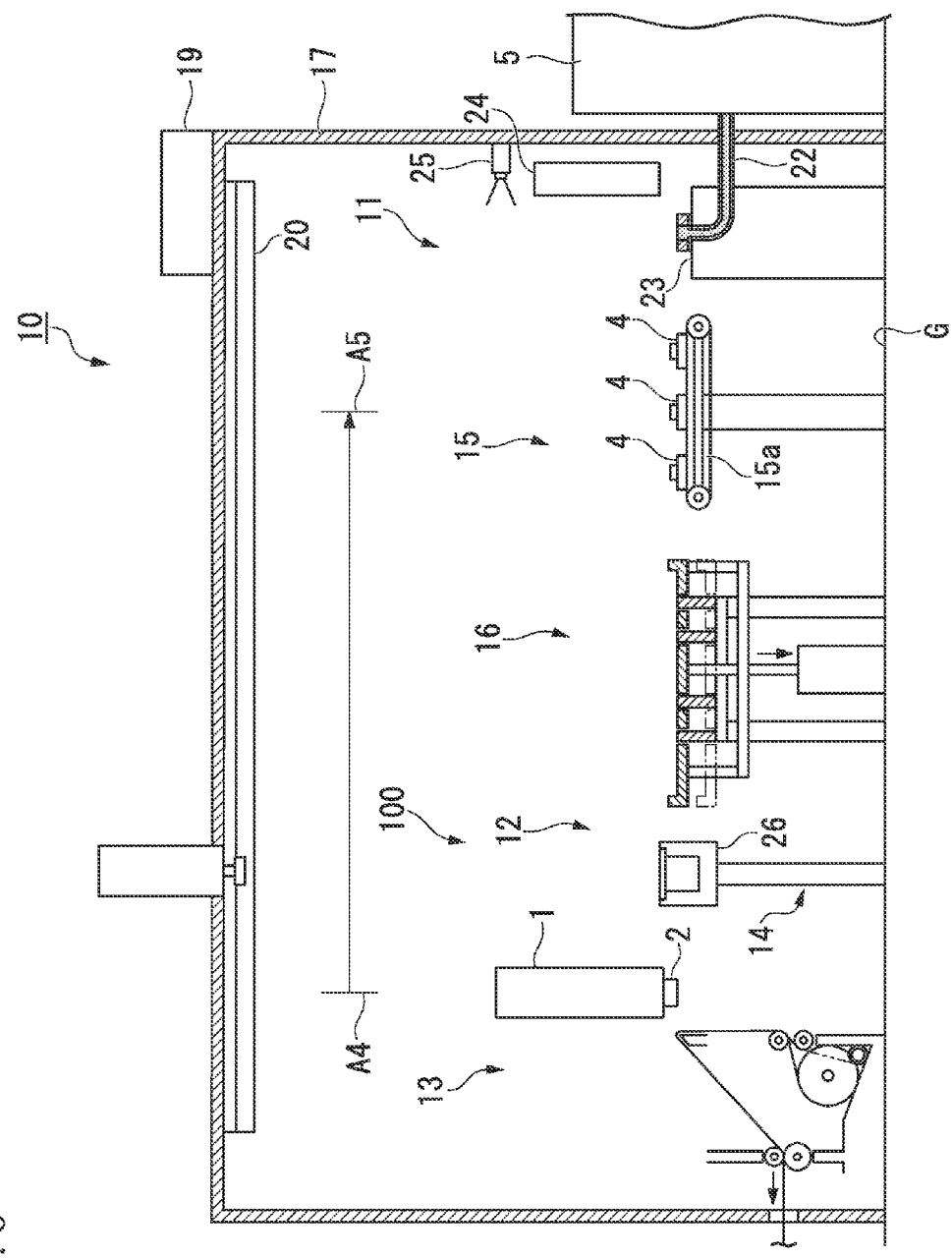
FIG. 6 is a side view schematically illustrating a weight-measuring step of the sealant-filling method performed by the sealant-filling apparatus shown in FIG. 1.

As shown in FIG. 6, when the sampling step is ended, the three-axis robot 20 holding the container 1 moves to the next position A5.

As shown in FIG. 7, a capping step is performed at the position A5 of the three-axis robot 20.

In the capping step, under the control of the controller 19, the container 1 is caused by the three-axis robot 20 to move down and the tip opening 2 of the container 1 with the inverted position in which the tip opening 2 faces down is covered with the cap 4 conveyed by the belt conveyor 15a.

When the capping step is ended, the three-axis robot 20 holding the container 1 moves to the next position A6.

As shown in FIG. 8, a direction-changing step is performed at the position A6 of the three-axis robot 20.

In the direction-changing step, under the control of the controller 19, the container 1 is arranged by the three-axis robot 20 so that the cap 4 is located on the falling concave portion 37 on the first support portion 35. Then, the robot hand 21 (see FIG. 3) of the three-axis robot 20 releases the container 1 and the container 1 is caused to fall down by the falling concave portion 37 so that the outer peripheral surface thereof is supported by the first support portion 35, whereby the direction thereof is changed to the horizontal direction. In this state, under the control of the controller 19, the first support portion 35 is caused to move down by the driving unit 38 and thus the container 1 is passed to the second support portion 36. The container 1 rolls to the storage unit 6 along the inclination of the second support portion 36. The container 1 rolling and being carried in the direction-changing step is stored in the cold storage 41 with the temperature maintained by the revolving door 40 in the storage unit 6 as shown in FIG. 2.

When the direction-changing step is ended, the three-axis robot 20 holding the container 1 is returned to the initial position A1 (see FIG. 3) and the above-mentioned steps are repeatedly performed, under the control of the controller 19.

In the sampling step for a next container 1, the controller 19 changes the position by a predetermined pitch in the width direction of the sampling paper sheet 29a by the use of the three-axis robot 20, and wipes out the sample sealant S2 with the sampling paper sheet 29a. When a predetermined number of sampling operations are performed at a predetermined pitch at the same position in the length direction of the sampling paper sheet 29a, the controller 19 drives the drawing unit 33 to draw out the sampling paper sheet 29a by a predetermined pitch and wipes out the sample sealant S2 with the sampling paper sheet 29a at a different position in the length direction, in the sampling step for a next container 1.

By repeating this operation, plural sample sealants S2 are sampled with the sampling paper sheet 29a at predetermined pitches in the width direction and the length direction.

Here, the controller 19 stores the data of the sampled container 1 read by the mark reader 24 and the sampling position on the sampling paper sheet 29a in correlation with each other. Accordingly, it is possible to identify what sample sealant S2 is correlated with what container 1 stored in the storage unit 6.

Accordingly, the controller 19 performs a load test for measuring an elastic coefficient or an appearance test for measuring the shape on the plural sample sealants S2 sampled with the sampling paper sheet 29a in a sample-inspecting step, and then can determine what container 1 is accepted or rejected on the basis of the test results.

As described above, according to the sealant-filling apparatus 10 including the sealant-inspecting apparatus 100 and the sealant-filling method including the sealant-inspecting method, it is possible to quantitatively evaluate the mixing state of air in the sealant S1 with which the container 1 is filled on the basis of the filled weight and the elastic force or shape of the sample sealant S2.

According to the sealant-inspecting apparatus 100 and the sealant-inspecting method, the sampling of the sample sealant S2 is performed by extracting a fixed amount of sample sealant S2 from the tip opening 2 of the container 1 in the sample-extracting step and by wiping off the sample sealant S2 with the sampling paper sheet 29a by the relative movement of the container 1 held by the three-axis robot 20 and the wiping unit 32. Therefore, it is not necessary to provide a complex apparatus configuration and it is possible to easily perform a sampling operation at low cost.

Accordingly, it is possible to easily perform a total inspection on the container 1 filled with the sealant S1.

The container filler-inspecting apparatus and the container filler-inspecting method according to the invention are not limited to the above-mentioned embodiment, but may be appropriately modified or improved in various forms.

For example, it has been stated in this embodiment that the sample sealant S2 is wiped out with the sampling paper sheet 29a by causing the container 1 to move relative to the wiping unit 32 by the use of the three-axis robot 20, but the invention is not limited to this configuration and the wiping unit 32 may be caused to move relative to the container 1.

The weight-measuring unit 14 is built in the lower part of the platform 26 and measures the weight at the same time as performing the sample-extracting step, but is not limited to this configuration. The weight-measuring step has only to be performed after the filling step is finished. The weight-measuring unit 14 may be built in the capping unit 15 and may measure the weight of the container 1 including the weight of the cap 4 after the capping step. Alternatively, the weight-measuring unit 14 may be built in the three-axis robot 20 and may measure the weight of the container 1 during carrying between the steps. The weight-measuring unit 14 may be independently provided and may measure the weight of the container 1 between any steps.

It is assumed in this embodiment that the filler is the two-liquid mixing type method of sealant, but the filler is not limited to such a type method. Where a container is filled with a filler having such predetermined viscosity to mix air therewith and being cured depending on the temperature or by a reaction with air and is stored, the invention can be applied to inspection of the mixing state of air in the filler.

INDUSTRIAL APPLICABILITY

By employing the container filler-inspecting apparatus and the container filler-inspecting method according to the invention, it is possible to easily inspect a filler with which a container is filled.

By employing the filling apparatus according to the invention, it is possible to fill a container with a filler while easily inspecting the filler.

REFERENCE SIGNS LIST

1: container
2: tip opening
10: sealant-filling apparatus (filling apparatus)
11: filling unit
12: sample-extracting unit
13: sampling unit
14: weight-measuring unit
15: capping unit
29a: sampling paper sheet
100 sealant-inspecting apparatus (container filler-inspecting apparatus)

The invention claimed is:

1. A container filler-inspecting apparatus, for inspecting a filler with which a container is filled by a fixed amount, the container filler-inspecting apparatus comprising:
a weight-measuring unit that measures a weight of the container filled with the filler;
a sample-extracting unit that extracts a fixed amount of filler from a tip opening of the container; and
a sampling unit that performs a sampling operation by wiping off the filler extracted by the sample-extracting unit with a sampling paper sheet,
wherein the sampling unit includes a wiping unit that forms a folded portion in the sampling paper sheet by folding the sampling paper sheet, and wipes off the filler with the sampling paper sheet by causing the container to move relative to the wiping unit.

2. The container filler-inspecting apparatus according to claim 1, wherein the sampling unit samples the filler from a plurality of the containers filled with the filler while sequentially changing its positions in a width direction and a length direction on the sampling paper sheet.

3. A filling apparatus comprising:
the container filler-inspecting apparatus according to claim 2;
a filling unit that fills the containers with the filler; and
a capping unit that caps the tip opening of the containers filled with the filler.

4. A filling apparatus comprising:
the container filler-inspecting apparatus according to claim 1;
a filling unit that fills the container with the filler; and
a capping unit that caps the tip opening of the container filled with the filler.

5. A container filler-inspecting method for inspecting a filler with which a container is filled by a fixed amount, container filler-inspecting method comprising:
a weight-measuring step of measuring a weight of the container filled with the filler;
a sample-extracting step of extracting a fixed amount of filler from a tip opening of the container; and
a sampling step of performing a sampling operation by wiping off the filler extracted in the sample-extracting step with a sampling paper sheet,
wherein the performing of the sampling operation includes forming a folded portion in the sampling paper sheet by folding the sampling paper sheet, and wiping off the filler with the sampling paper sheet by causing the container to move relative to the wiping unit.

* * * * *